United States Patent
Tsugita

[19]

[11] Patent Number: 6,142,987
[45] Date of Patent: Nov. 7, 2000

[54] GUIDED FILTER WITH SUPPORT WIRE AND METHODS OF USE

[75] Inventor: Ross S. Tsugita, Mountain View, Calif.

[73] Assignee: SciMed Life Systems, Inc., Maple Grove, Minn.

[21] Appl. No.: 09/366,192

[22] Filed: Aug. 3, 1999

[51] Int. Cl.[7] .................................................. A61M 29/00
[52] U.S. Cl. ..................... 604/500; 604/509; 604/96.01; 606/194
[58] Field of Search ..................................... 604/500, 523, 604/532, 508, 509, 96.01, 104, 105, 106, 107; 606/200, 198, 194, 191

[56] References Cited

U.S. PATENT DOCUMENTS

| | | |
|---|---|---|
| 4,873,978 | 10/1989 | Ginsburg . |
| 5,053,008 | 10/1991 | Bajaj . |
| 5,662,671 | 9/1997 | Barbut . |
| 5,749,848 | 5/1998 | Jang . |
| 5,769,816 | 6/1998 | Barbut . |

FOREIGN PATENT DOCUMENTS 34 17 738  11/1985  Germany .

OTHER PUBLICATIONS

Waksman, et al., *American Heart Journal* 129(3):430–435 (1995).
Jordan, et al., *Cardiovascular Surgery* 7(1):33–38 (1999).
*American Heart Journal* 125(2 pt 1):362–366 (1993).

*Primary Examiner*—John D. Yasko
*Attorney, Agent, or Firm*—Crompton, Seager & Tufte, LLC

[57] ABSTRACT

A guided filter system for temporary placement of a filter in an artery or vein is disclosed. The system includes a guidewire slideable through a wire guide included in a distal region of a support wire. The support wire has an expandable filter, which is operable between a collapsed or enlarged condition. A variety of endovascular devices, including angioplasty, atherectomy, and stent-deployment catheters, are insertable over the guidewire and/or the support wire. Methods of using the guided filter system to direct and exchange endovascular devices to a region of interest, and to entrap and remove embolic material from the vessel are also disclosed.

31 Claims, 4 Drawing Sheets

*Fig.1J*
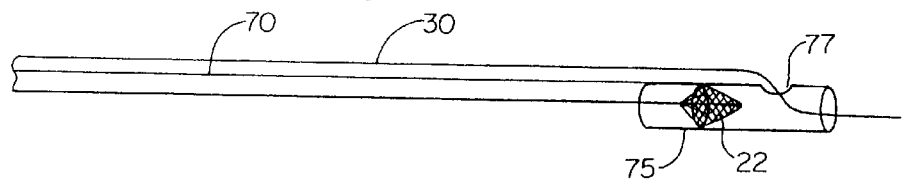
*Fig.1K*
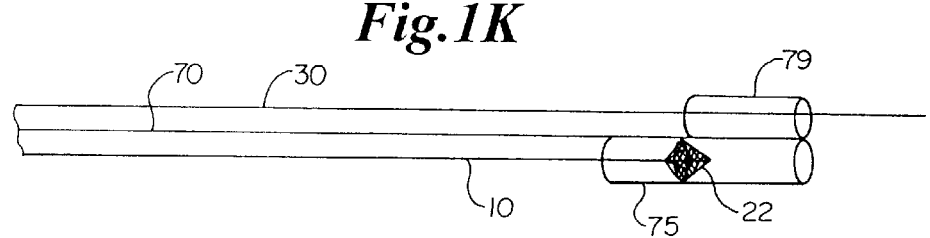
*Fig. 2A*  *Fig. 2B*  *Fig. 2C*
 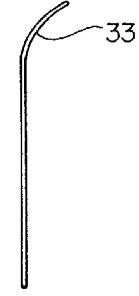 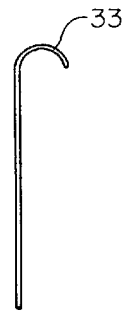
*Fig. 3A*
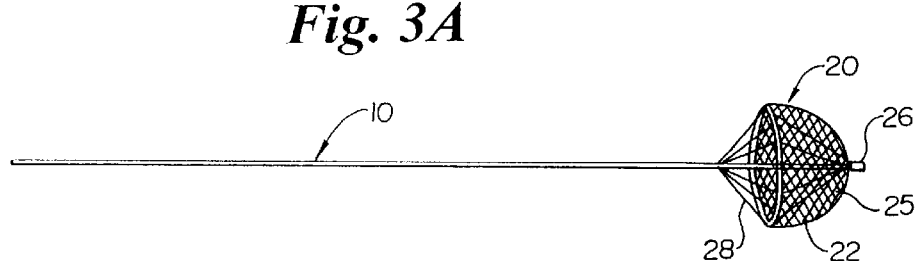
*Fig. 3B*
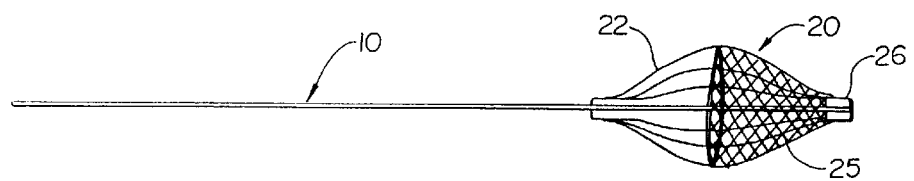

GUIDED FILTER WITH SUPPORT WIRE AND METHODS OF USE

FIELD OF THE INVENTION

The present invention relates generally to devices and methods for providing temporary placement of a filter in a blood vessel. More particularly, the invention provides a guidewire system for entrapment of embolic material in an artery or vein during an endovascular procedure. The system also provides a support wire for directing and/or exchanging other "over the wire" devices, such as angioplasty, atherectomy, or stent deployment catheters, to a region of interest within the vessel.

BACKGROUND OF THE INVENTION

Treatment of thrombotic or atherosclerotic lesions in blood vessels using an endovascular approach has recently proven to be an effective and reliable alternative to surgical intervention in selected patients. For example, directional atherectomy and percutaneous translumenal coronary angioplasty (PTCA) with or without stent deployment are useful in treating patients with coronary occlusion. Atherectomy physically removes plaque by cutting, pulverizing, or shaving in atherosclerotic arteries using a catheter-deliverable endarterectomy device. Angioplasty enlarges the lumenal diameter of a stenotic vessel by exerting mechanical force on the vascular walls. In addition to using angioplasty, stenting, and/or atherectomy on the coronary vasculature, these endovascular techniques have also proven useful in treating other vascular lesions in, for example, carotid artery stenosis, peripheral arterial occlusive disease (especially the aorta, the iliac artery, and the femoral artery), renal artery stenosis caused by atherosclerosis or fibromuscular disease, superior vena cava syndrome, and occlusive iliac vein thrombosis resistant to thrombolysis.

It is well recognized that one of the complications associated with endovascular techniques is the dislodgment of embolic materials generated during manipulation of the vessel, thereby causing occlusion of the narrower vessels downstream and ischemia or infarct of the organ which the vessel supplies. In 1995, Waksman et al. disclosed that distal embolization is common after directional atherectomy in coronary arteries and saphenous vein grafts. See Waksman et al., American Heart Journal 129(3): 430-5 (1995), incorporated herein by reference. This study found that distal embolization occurs in 28% (31 out of 111) of the patients undergoing atherectomy. In January 1999, Jordan, Jr. et al. disclosed that treatment of carotid stenosis using percutaneous angioplasty with stenting is associated with more than eight times the rate of microemboli seen using carotid endarterectomy. See Jordan, Jr. et al. Cardiovascular surgery 7(1): 33-8 (1999), incorporated herein by reference. Microemboli, as detected by transcranial Doppler monitoring in this study, have been shown to be a potential cause of stroke. The embolic materials include calcium, intimal debris, atheromatous plaque, thrombi, and/or air.

There are a number of devices designed to provide blood filtering for entrapment of vascular emboli. The vast majority of these devices are designed for permanent placement in veins to prevent pulmonary embolism. A temporary venous filter device is disclosed in Bajaj, U.S. Pat. No. 5,053,008 (this and all other references cited herein are expressly incorporated by reference as if fully set forth in their entirety herein). The Bajaj device is an intracardiac catheter for temporary placement in the pulmonary trunk of a patient predisposed to pulmonary embolism due to, e.g., hip surgery, major trauma, major abdominal or pelvic surgery, or immobilization. The Bajaj device includes an umbrella made from meshwork which traps venous emboli before they reach the lungs. This device is designed for venous filtration and is not suitable for arterial use because of the hemodynamic differences between arteries and veins.

There are very few intravascular devices designed for arterial use. Arteries are much more flexible and elastic than veins and, in the arteries, blood flow is pulsatile with large pressure variations between systolic and diastolic flow. These pressure variations cause the artery walls to expand and contract. Blood flow rates in the arteries vary from about 1 to about 5 L/min. Ginsburg, U.S. Pat. No. 4,873,978, discloses an arterial filtering system, which includes a catheter with a strainer device at its distal end. This device is inserted into the vessel downstream from the treatment site and, after treatment, the strainer is collapsed around the entrapped emboli and removed from the body. The Ginsburg device could not withstand flow rates of 5 L/min. It is designed for only small arteries and therefore could not capture emboli destined for all parts of the body. Ing. Walter Hengst GmbH & Co, German Patent DE 34 17 738, also discloses another arterial filter having a folding linkage system which converts the filter from the collapsed to the expanded state.

Filters mounted to the distal end of guidewires have been proposed for intravascular blood filtration. A majority of these devices includes a filter which is attached to a guidewire and is mechanically actuated via struts or a pre-shaped basket which deploys in the vessel. These filters are typically mesh "parachutes" which are attached to the shaft of the wire at the distal end and to wire struts which extend outward in a radial direction at their proximal end. The radial struts open the proximal end of the filter to the wall of the vessel. Blood flowing through the vessel is forced through the mesh thereby capturing embolic material in the filter. These devices are self-directing and can be placed intravascularly. However, one major disadvantage associated with the current devices is that the steerability of the guidewire may be altered as compared to the conventional guidewires due to the size of the filter. The guidewire may bend, kink, and/or loop around in the vessel, making insertion of the filter through a complex vascular lesion difficult.

During endovascular procedures, it is not uncommon to exchange one endovascular device for another over the guidewire. However, the guidewire position is often lost or compromised during the exchange of devices. For example, during coronary revascularization, it is often required to exchange of one guide catheter for another guide catheter possessing different qualities, e.g., a larger diameter guide to deliver a specialized angioplasty device, a smaller diameter guide to prevent deep intubation and/or pressure damping, a different guide shape, or a guide catheter containing side holes. It is known that there are few interventional maneuvers as challenging as attempting to maintain distal guidewire access while trying to exchange one guiding catheter for another without compromising the guidewire position.

What is needed are simple and safe blood filtering and guidewire systems which can be temporarily placed in the arteries and veins to prevent distal embolization during endovascular procedures, and can be used to introduce and/or exchange various instruments to a region of interest without compromising the position of the filter or guidewire. Existing devices are inadequate for this purpose.

SUMMARY OF THE INVENTION

The present invention provides devices and methods for introduction of endovascular devices, e.g., guide catheters, atherectomy catheters, angioplasty catheters, intravascular ultrasound catheters, or stent-deployment catheters, and for protecting a patient from distal embolization during cardiovascular procedures. More specifically, a guided filter system with support wire is disclosed for capturing embolic material generated during the procedure and for directing or exchanging other devices to a region of interest in an artery or vein.

In one embodiment, the filter system comprises a guidewire and a support wire having an expandable filter, e.g., a parachute, basket, or scroll, mounted on a distal region of the support wire. The support wire is adapted for percutaneous insertion into an artery or vein and is adapted to receive an endovascular instrument. The distal region of the support wire includes a wire guide, which slideably engages the guidewire. In certain embodiments, the wire guide comprises a ring having an aperture adapted to receive the guidewire.

In another embodiment, the filter comprises an expansion frame and a mesh disposed over the frame. The filter can be placed in a collapsed condition to facilitate entry into a vessel and an enlarged condition to capture embolic material in the vessel. In certain embodiments, the frame comprises a plurality of struts bonded to the guidewire at a first end, and the struts expand radially outward at a second end. The construction and use of expansion means and associated filter mesh have been thoroughly discussed in earlier applications including Barbut et al., U.S. application Ser. No. 08/533,137, filed Nov. 7, 1995, Barbut et al., U.S. application Ser. No. 08/580,223, filed Dec. 28, 1995, Barbut et al., U.S. application Ser. No. 08/584,759, filed Jan. 9, 1996, Barbut et al., U.S. application Ser. No. 08/640,015, now U.S. Pat. No. 5,769,816 filed Apr. 30 1996, Barbut et al., U.S. application Ser. No. 08/645,762, filed May 14, 1996, and Barbut et al., U.S. Pat. No. 5,662,671, and the contents of each of these prior applications are expressly incorporated herein by reference.

The methods of the present invention include deployment of a percutaneous medical instrument during an endovascular procedure to remove plaque and/or thrombi from the coronary artery, aorta, common carotid artery, external and internal carotid arteries, brachiocephalic trunk, middle cerebral artery, basilar artery, subclavian artery, brachial artery, axillary artery, iliac artery, renal artery, femoral artery, popliteal artery, celiac artery, superior mesenteric artery, inferior mesenteric artery, anterior tibial artery, posterior tibial artery, and all other arteries carrying oxygenated blood. The methods also include prevention of distal embolization during an endovascular procedure to remove thrombi and/or foreign bodies in the venous circulation, including the superior vena cava, inferior vena cava, external and internal jugular veins, brachiocephalic vein, pulmonary artery, subclavian vein, brachial vein, axillary vein, iliac vein, renal vein, femoral vein, profunda femoris vein, great saphenous vein, portal vein, splenic vein, hepatic vein, and azygous vein.

In a first method of using the guided filter system, the distal end of the guidewire is inserted percutaneously through an artery or vein and advanced into or beyond a region of interest, typically a stenotic lesion caused by buildup of atherosclerotic plaque and/or thrombi. In a collapsed condition, the filter and the distal region of the support wire are advanced over the guidewire, having the wire guide of the support wire engaging the guidewire, i.e., like a monorail catheter engaging a guidewire. The filter is expanded downstream of the vascular occlusion, and the guidewire is withdrawn and removed from the body. The distal region of an endovascular device, such as an atherectomy, stent-deployment, or angioplasty catheter, is inserted over the support wire and advanced to the region of interest. After the stenotic lesion is removed or otherwise treated by the endovascular device and an adequate lumenal diameter is established, the filter is collapsed and removed, together with the captured embolic debris, from the vessel by withdrawing the support wire.

In another method, after the guidewire and the support wire with the expanded filter are positioned in a vessel distal to the region of interest, the endovascular device is inserted over both the guidewire and the support wire to position within the region of interest. During certain cardiovascular procedures, especially coronary revascularization, exchange of endovascular instruments and catheters is needed and is difficult to accomplish because the initial guidewire positioning across the region of interest is often lost as the first device is withdrawn. Using the guided filter system, the guidewire and the support wire are both advanced distal to the region of interest. If the position of the guidewire is lost during the withdrawal of the first device, the second device that needs to be exchanged can be advanced over the support wire to be positioned within the region of interest.

It will be understood that there are several advantages in using the devices and methods disclosed herein for capturing and removing embolic debris during endovascular procedures. For example, the guided filter system (1) is particularly well suited for temporary filtration of blood in any vessel to entrap embolic debris, thereby minimizing neurologic, cognitive, and cardiac complications associated with distal embolization, (2) can withstand high arterial blood flow for an extended time, (3) includes a mesh that is sufficiently porous to allow adequate blood flow in a blood vessel while capturing emboli, (4) can be used to direct an endovascular catheter to a region of interest in the vessel, (5) can be used to exchange medical instruments without compromising the position of the guidewire, and (6) can be used in adult and pediatric patients.

BRIEF DESCRIPTION OF THE DRAWINGS

FIG. 1J depicts the guidewire and the support wire carried within a rapid exchange catheter.

FIG. 1K depicts the guidewire and the support wire carried within a rapid exchange catheter.

FIG. 2A depicts an embodiment of a distal end of the guidewire.

FIG. 2B depicts an alternative embodiment of the distal end of the

FIG. 2C depicts another alternative embodiment of the distal end of the guidewire.

FIG. 3A depicts another embodiment of the filter shaped as a parachute.

FIG. 3B depicts another embodiment of the filter shaped as an eggbeater.

DETAILED DESCRIPTION

Figure 1A:
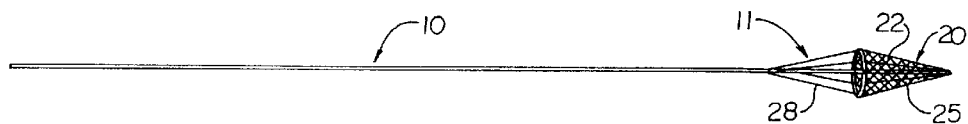
FIG. 1A depicts an embodiment of a support wire having a filter in a collapsed condition according to the present invention.
Figure 1B:
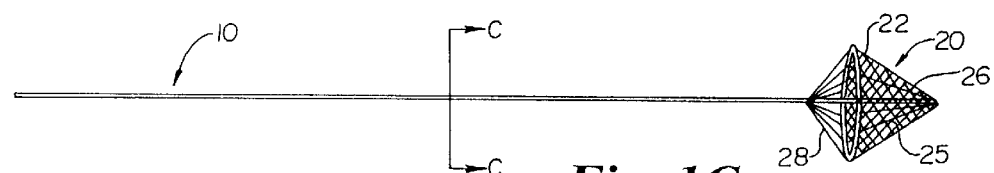
FIG. 1B depicts the support wire of FIG. 1A having the filter in an expanded condition.
Figure 1C:
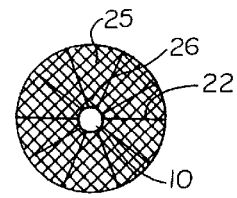
FIG. 1C depicts a cross-sectional view through section line C—C of the support wire depicted in FIG. 1B.
Figure 1D:
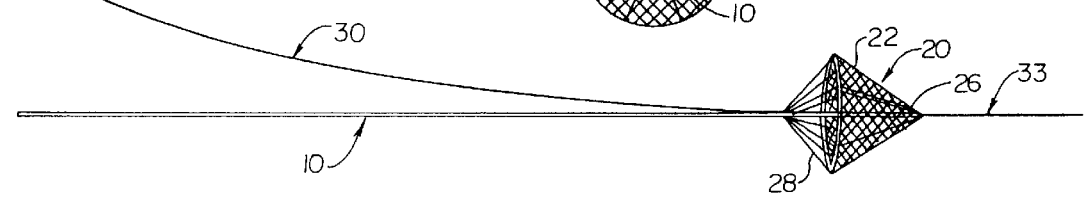
FIG. 1D depicts the support wire of FIG. 1C having a guidewire received through the wire guide mounted within the filter.
Figure 1E:
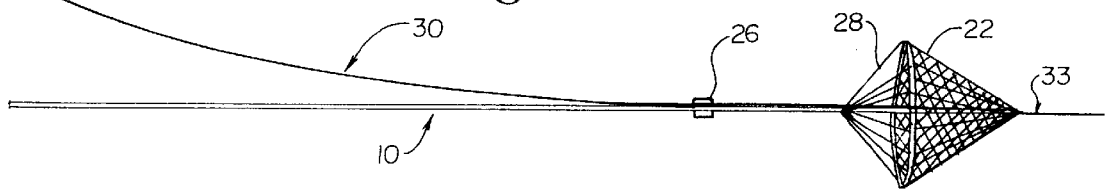
FIG. 1E depicts the support wire of FIG. 1C having a guidewire received through the wire guide mounted proximal to the filter.
Figure 1F:
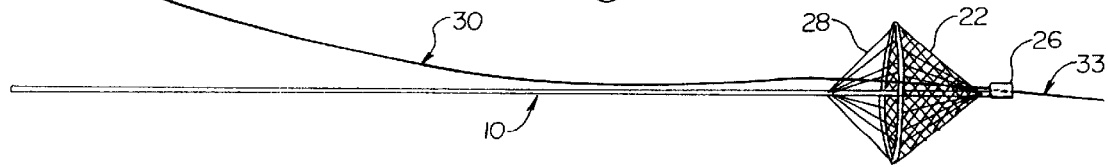
FIG. 1F depicts the support wire of FIG. 1C having a guidewire received through the wire guide mounted distal to the filter.

In a first embodiment, a filter system for temporary placement in a vessel, either an artery or vein, is provided as depicted in FIGS. 1A, 1B, 1C, and 1D. The filter system includes support wire 10 having a proximal end, distal region 11, and expandable filter 20 mounted at the distal region. The filter comprises expansion frame 22 and mesh 25 which is sonic welded or adhesive bonded to struts 28 of the expansion frame. Anticoagulants, such as heparin and heparinoids, may be applied to mesh 25 to reduce thrombi formation on the mesh. The filter can be collapsed as shown in FIG. 1A to facilitate insertion into a vessel, and thereafter expanded as shown in FIG. 1B. Wire guide 26 is included in distal region 11 of the support wire. The wire guide may be mounted within the filter (as shown in FIG. 1B and FIG. 1C) or at any other suitable position on support wire 10 proximal of the filter (as shown in FIG. 1E), or on a distal extension of the support wire which extends beyond the filter (as shown in FIG. 1F). In certain embodiments, the support wire may comprise a ring. A cross-sectional view of the support wire through section line C—C is depicted in FIG. 1C. The design and construction of a variety of filters for use on guidewire is described in detail in Tsugita et al., U.S. Pat. No. 5,911,734, the disclosure of which is expressly incorporated herein by reference in its entirety.

Figure 1G:
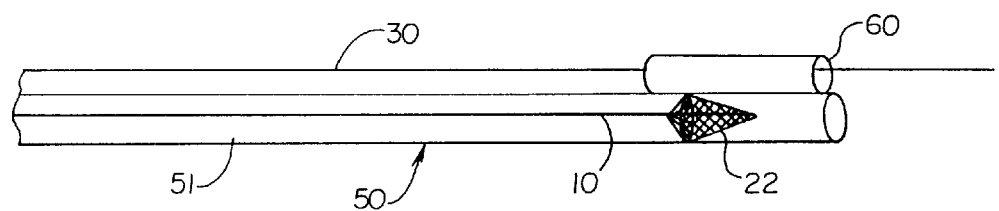
FIG. 1G depicts the guidewire and the support wire carried within a rapid exchange catheter.
Figure 1I:
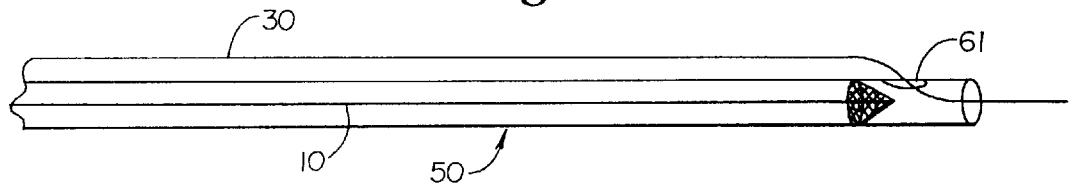
FIG. 1I depicts the guidewire and the support wire carried within a rapid exchange catheter.

In another embodiment, the filter further includes a capture sheath which covers the filter and is removeable from the filter, the sheath having a port in its distal region adapted to receive the guidewire in the manner of a rapid exchange catheter. In FIG. 1G, support wire 10 is inserted in lumen 51 of a rapid exchange catheter 50. The catheter includes side port 60 in its distal region, adapted to receive guidewire 30. In FIG. 1I, the catheter includes skive 61 which receives guidewire 30. In FIG. 1J, elongate member 70 carries tubular segment 75 having skive 77 at a distal region of elongate member 70. The tubular segment acts as a capture sheath for the filter while the skive receives the guidewire. In FIG. 1K, elongate member 70 carries first and second tubular segments, 75 and 79, adapted to receive, respectively, the filter and the guidewire.

Figure 1H:
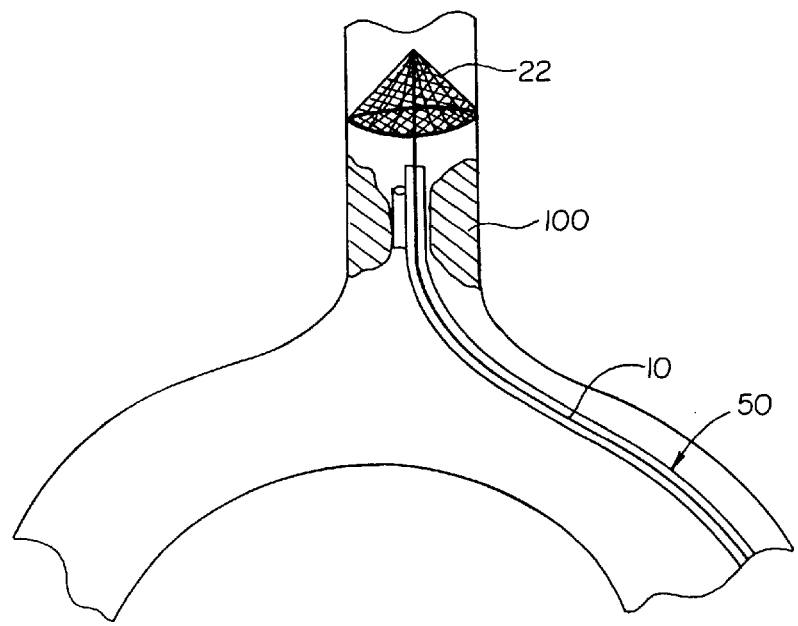
FIG. 1H depicts the catheter of FIG. 1 G deployed over an atheromatous lesion in a vessel.

When in use, guidewire 30 is first inserted into a vessel and advanced distal to the region of interest. The catheter, which carries the filter in lumen 51, is inserted over the guidewire, the guidewire engaged through side port 60. The filter is advanced distally passing atheromatous lesion 100. The guidewire can then be withdrawn and catheter 50 drawn proximal, leaving the catheter and the filter inserted in the vessel as depicted in FIG. 1H. Catheter 50 is then removed from the vessel. Expansion frame 22 is expanded to capture embolic materials downstream the atheromatous lesion. An endovascular device, such as an angioplasty catheter with or without a stent, can be inserted over support wire 10 to position adjacent atheroma 100.

After vascular procedures are performed with the endovascular device(s), the device(s) are withdrawn and removed from the vessel. The filter with the captured emboli is then contracted and removed.

The filter system also includes guidewire 30 having a proximal end and distal end 33. The guidewire is slideably received by support wire 10 through wire guide 26 as depicted in FIG. 1D. The filter system further includes endovascular devices, such as atherectomy catheters, endovascular imaging devices, stent-deployment catheters, angioplasty catheters, pressure monitors, electrophysiology catheters, and aspirators, which are adapted to receive guidewire 30 and/or support wire 10 in their lumens.

Different constructions of distal end 33 of the guidewire are depicted in FIGS. 2A, 2B, and 2C. Distal end 33 may assume a substantially linear configuration relative to the proximal end of the guidewire as depicted in FIG. 2A. Alternatively, distal end 33 may assume an angular configuration relative to the proximal end of the guidewire as depicted in FIG. 2A. Distal end 33 may be shaped like a fishhook as depicted in FIG. 2C. The distal region of the guidewire may be constructed of a flexible material to facilitate entry through a region of interest, and preferably is equipped with an atraumatic tip as is known in the art. The embodiments in FIGS. 2B and 2C, having a curvilinear design, are particularly useful in achieving access to a complex lesion in a tortuous vessel.

FIGS. 3A and 3B depict alternative embodiments of expandable filter 20 mounted on the distal region of support wire 10. In FIG. 3A, filter 20 comprises a parachute frame, and mesh 25 which is welded (e.g., sonic or laser) or adhesive bonded to struts 28. Wire guide 26 is included in the distal region of the support wire and projects distally from filter 20 for engaging a guidewire. In FIG. 3B, filter 20 comprises compressible struts 22, and mesh 25. In an expanded condition, filter 20 assumes the shape of an eggbeater.

By way of example, when the filter system as disclosed herein is intended for use in the aorta, the area of the mesh required for the device is calculated from Bernoulli's equation as described in our earlier applications including Barbut et al., U.S. application Ser. No., U.S. application Ser. No. 08/553,137, filed Nov. 7, 1995, Barbut et al., U.S. application Ser. No. 08/580,223, filed Dec. 28, 1995, Barbut et al., U.S. application Ser. No. 08/584,759, filed Jan. 9, 1996, Barbut et al., U.S. application Ser. No. 08/640,015, filed Apr. 30, 1996, and Barbut et al., and U.S. application Ser. No. 08/645,762, filed May 14, 1996, all of which are incorporated herein by reference.

In an embodiment of the guided filter system that is to be used in the aorta, mesh with dimensions within the following ranges is desirable: mesh area is 0.004–5 in more preferably 0.007–4 $in^2$, more preferably 0.010–3 $in^2$, more preferably 0.015–2 $in^2$, more preferably 0.020–1 $in^2$, more preferably 0.025–0.076 $in^2$; mesh thickness is 60–280 $\mu$m, more preferably 70–270 $\mu$m, more preferably 80–260 $\mu$m, more preferably 90–250 $\mu$m, more preferably 100–250 $\mu$m, more preferably 120–230 $\mu$m, more preferably 140–210 $\mu$m;

thread diameter is 30–145 μm, more preferably 40–135 μm, more preferably 50–125 μm, more preferably 60–115 μm, more preferably 70–105 μm, and pore size is 500 μm or less, more preferably 400 μm or less, more preferably 300 μm or less, more preferably 200 μm or less, more preferably 100 μm or less, more preferably 50 μm or less and usually larger than at least a red blood cell. In a preferred embodiment of the invention, mesh area is 2–8 in$^2$, mesh thickness is 60–200 μm, thread diameter is 30–100 μm, and pore size is 50–300 μm. In a further preferred embodiment of the invention, mesh area is 3–5 in$^2$, mesh thickness is 60–150 μm, thread diameter is 50–80 μm, and pore size is 100–250 μm. In other embodiments, the filter comprises a thin film laser cut with holes to allow blood flow. Typical dimensions include pore size of 20–500 μm, a thickness of 0.0005–0.003 inches, and area approximately same as for meshes described above.

In other embodiments, the filter comprises a thin film laser cut with holes to allow blood flow. Typical dimensions include pore size of 20–500 μm, a thickness of 0.0005–0.003 inches, and area approximately same as for meshes described above .

Once appropriate physical characteristics are determined, suitable mesh can be found among standard meshes known in the art. For example, polyester meshes may be used, such as meshes made by Saati Corporations and Tetko Inc. These are available in sheet form and can be easily cut and formed into a desired shape. In a preferred embodiment, the mesh is welded (e.g. sonic or laser) or sewn into a cone shape. Other meshes known in the art, which have the desired physical characteristics, are also suitable. Anticoagulants, such as heparin and heparinoids, may be applied to the mesh to reduce the chances of blood clotting on the mesh. Anticoagulants other than heparinoids also may be used, e.g., monoclonal antibodies such as ReoPro (Centocor). The anticoagulant may be painted or sprayed onto the mesh. A chemical dip comprising the anticoagulant also may be used. Other methods known in the art for applying chemicals to mesh may be used.

Figure 4A:
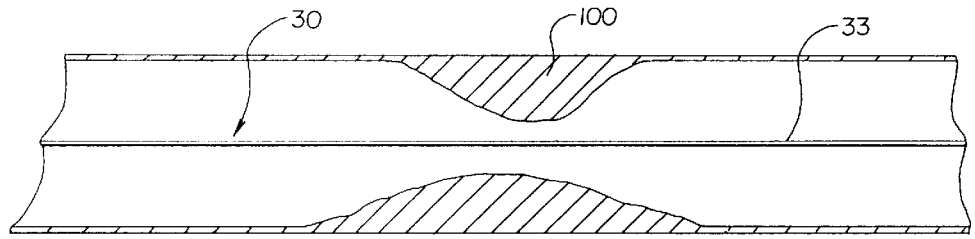
FIG. 4A depicts a guidewire inserted across a vascular occlusion.
Figure 4B:
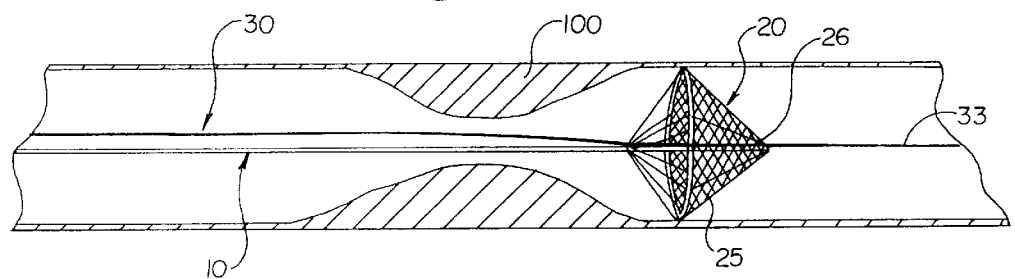
FIG. 4B depicts the filter and support wire engaging the guidewire with the filter expanded beyond the vascular occlusion.

In use, as depicted in FIG. 4A, guidewire 30 is inserted percutenously through a peripheral artery or vein and advanced typically in the direction of blood flow. However, guidewire 30 may be inserted and advanced in a direction opposite the blood flow, e.g., retrograde through the descending aorta to reach the coronary artery. Distal end 33 of the guidewire is passed through occluding lesion 100, typically an atheromatous plaque, and positioned distal to the occlusion. Support wire 10 of FIG. 1A is inserted over the proximal end of guidewire 30 through wire guide 26, and advanced distally until filter 20 is positioned distal to plaque 100 as depicted in FIG. 4B. By having wire guide 26 engage the guidewire, the filter and the support wire can be easily steered intravascularly to reach the region of interest. Filter 20 is expanded to capture embolic material, such as calcium, thrombi, plaque, and/or tissue debris. Guidewire 30 is then withdrawn, leaving support wire 10 in position to direct an endovascular device to plaque 100.

Figure 4C:
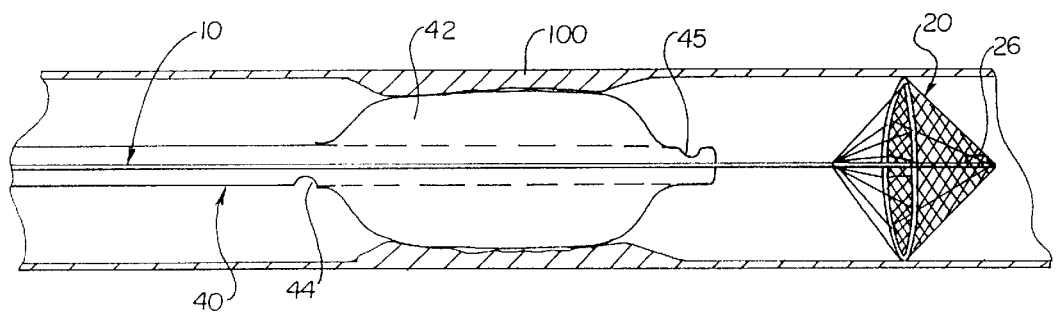
FIG. 4C depicts an angioplasty catheter inserted over the support wire.

Percutaneous translumenal angioplasty has been successful in treating arterial stenoses as well as occlusive venous thrombosis resistant to thrombolysis. See American Heart Journal, 125 (2 Pt 1): 362-6 (1993). Angioplasty catheter 40, which has angioplasty balloon 42 mounted on the distal region, is inserted over support wire 10 as depicted in FIG. 4C. In a deflated state, the angioplasty balloon is advanced over support wire 10 to a position adjacent plaque 100. The atheromatous plaque is compressed by inflating balloon 42, thereby dilating the stenosis in the vessel. In certain embodiments, the angioplasty catheter includes infusion port 44 proximal and perfusion port 45 distal to balloon 42. Infusion port 44 may be used to administer pharmaceutical agents, e.g., tPA, adenosine, or nitroglycerin through the catheter lumen (not shown). Oxygenated medium or blood may be infused through port 45 to maintain perfusion to distal organs during angioplasty. In certain embodiments, a stent is closely associated with the angioplasty balloon. The stent is typically crimped onto the balloon and is capable of controlled radial expansion in the region of interest upon application of a radial, outwardly extending force from the interior of the stent. The construction of the catheter system carrying a stent is described in detail in Jang et al., U.S. Pat. No. 5,749,848, which is incorporated herein by reference in its entirety.

The angioplasty catheter or other endovascular instrument is withdrawn from the vessel after completion of angioplasty. Embolic material generated during the angioplasty is captured and retained by filter 20. The filter is then contracted, and with captured embolic material, is withdrawn from the vessel and removed from the patient's body.

Figure 4D:
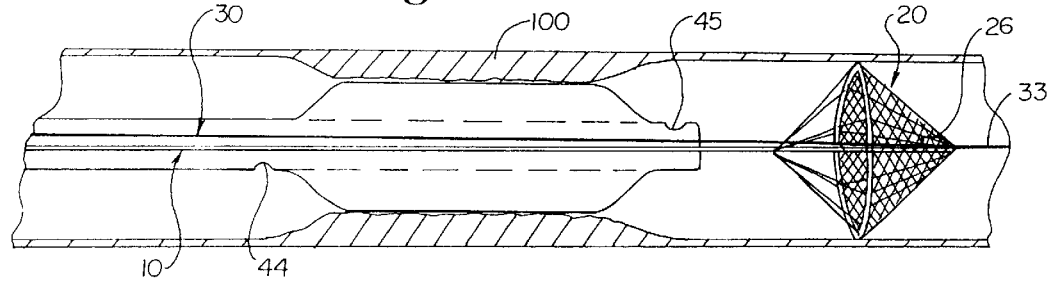
FIG. 4D depicts an angioplasty catheter inserted over the guidewire and the support wire.

Alternatively, after filter 20 is positioned and expanded distal to plaque 100, guidewire 30 and support wire 10 may remain in the vessel across plaque 100 as depicted in FIG. 4D. Angioplasty catheter 40 is then inserted over both guidewire 30 and support wire 10 to a position adjacent plaque 100. If an atherectomy device, for example, is required to remove plaque remaining after angioplasty, angioplasty catheter 40 is withdrawn, with or without the guidewire, and an atherectomy catheter is inserted over guidewire 30 and/or support wire 10 to a position adjacent the plaque. In this way, if the position of guidewire 30 across the plaque is lost during the removal of angioplasty catheter 40, support wire 10 is available to direct another endovascular device to the region of interest. This method is particularly useful for exchanging guide catheters during coronary revascularization.

The length of the guidewire and the support wire will generally be between 30 and 300 centimeters, preferably approximately between 50 and 180 centimeters. The filter will be capable of expanding to an outer diameter of at least 0.2 centimeters, more preferably at least 0.5 centimeters, more preferably at least 1.0 centimeters, more preferably at least 1.5 centimeters, more preferably at least 2.0 centimeters, more preferably at least 2.5 centimeters, more preferably at least 3.0 centimeters, more preferably at least 3.5 centimeters, more preferably at least 4.0 centimeters, more preferably at least 4.5 centimeters, more preferably at least 5.0 centimeters. These ranges cover suitable diameters for both pediatric and adult use. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for the purposes of clarity and understanding, been described in some detail by way of illustration and example, it will be obvious that certain changes and modifications may be practiced which will still fall within the scope of the appended claims. Moreover, it will be understood that each and every feature described for any given embodiment or in any reference incorporated herein, can be combined with any of the other embodiments described herein.

What is claimed is:

1. A method for deploying a percutaneous medical instrument, comprising the steps of:

providing a guidewire and a support wire, the support wire having a distal region, a wire guide mounted on the distal region, and an expandable filter mounted on the distal region;

advancing the guidewire into a region of interest within a vessel;

advancing the support wire along the guidewire with the wire guide of the support wire engaging the guidewire;

expanding the filter downstream of the region of interest; and advancing the percutaneous medical instrument over the support wire and positioning the medical instrument within the region of interest.

2. The method of claim 1, further comprising the step of removing the guidewire from the vessel.

3. The method of claim 1, wherein the region of interest is within a coronary artery.

4. The method of claim 1, wherein the region of interest is within a carotid artery.

5. The method of claim 1, wherein the region of interest contains atheromatous plaque.

6. The method of claim 1, wherein the wire guide comprises a ring having an aperture adapted to receive the guidewire.

7. The method of claim 1, wherein the percutanous medical instrument is an angioplasty balloon catheter.

8. The method of claim 1, wherein the percutanous medical instrument is a stent-deployment catheter.

9. The method of claim 8, wherein the stent-deployment catheter comprises a sheath disposed about a self-expanding stent.

10. The method of claim 1, wherein the percutanous medical instrument is an atherectomy catheter.

11. The method of claim 1, wherein the percutanous medical instrument is an aspiration catheter.

12. The method of claim 7, further comprising the step of inflating the angioplasty balloon at the region of interest, wherein embolic material is captured by the filter.

13. The method of claim 8, further comprising the step of expanding the stent at the region of interest, wherein embolic material is captured by the filter.

14. The method of claim 1, further comprising the step of:

contracting the filter; and removing the support wire from the vessel.

15. The method of claim 1, further comprising the step of removing the percutaneous medical instrument from the vessel.

16. The method of claim 1, wherein the expandable filter comprises a plurality of struts and a mesh disposed about the struts.

17. The method of claim 1, wherein the filter expands to the shape of an eggbeater.

18. The method of claim 1, further comprising the step of exchanging one percutanous medical instrument for another.

19. A percutaneous filter system, comprising:

a guidewire;

a support wire having a proximal end, a distal end, and a distal region, the support wire adapted to receive a percutaneous medical instrument;

an expandable filter mounted on the distal region of the support wire; and a wire guide mounted on the distal region of the support wire and slideably engaging the guidewire, wherein, during use, the guidewire is positioned in a vessel at a region of interest, and the support wire is advanced along the guidewire until the filter reaches the region of interest.

20. The system of claim 19, wherein the expandable filter is manually activated.

21. The system of claim 19, wherein the expandable filter is selfactivating.

22. The system of claim 19, wherein the wire guide comprises a ring having an aperture adapted to receive the guidewire.

23. The system of claim 19, wherein the expandable filter comprises a plurality of struts and a mesh disposed about the struts.

24. The system of claim 23, wherein the mesh is woven.

25. The system of claim 23, wherein the mesh is a thin film having holes to allow fluid flow.

26. The system of claim 19, wherein the filter expands to the shape of an eggbeater.

27. The system of claim 19, further comprising a percutaneous medical instrument selected from the group consisting of an angioplasty catheter, a stent-deployment catheter, an atherectomy catheter, intravascular ultrasound catheter, and an aspiration catheter.

28. The system of claim 27, wherein the stent-deployment catheter comprises a sheath disposed about a self-expanding stent.

29. The method of claim 1, wherein the wire guide is mounted on the support wire within the filter.

30. The method of claim 1, wherein the wire guide is mounted on the support wire distal the filter.

31. A percutaneous filter system, comprising:

a guidewire;

a support wire having a proximal end, a distal end, a distal region, and an expandable filter mounted on the distal region of the support wire, the support wire adapted to receive a percutaneous medical instrument; and a sheath which removeably covers the support wire and filter, the sheath having a proximal end, a distal end, and a distal region, the distal region having a lumen which receives the filter and an aperture adapted to pass the guidewire, wherein, during use, the guidewire is positioned in a vessel at a region of interest, the sheath carrying the support wire is advanced along the guidewire until the filter reaches the region of interest, and the sheath is withdrawn to expose the filter.

* * * * *